United States Patent [19]

Miller

[11] 4,126,124
[45] Nov. 21, 1978

[54] METHOD OF SIZING A HAIR ANCHOR

[75] Inventor: Paul W. Miller, Atlanta, Ga.

[73] Assignee: Hairegenics, Inc., Atlanta, Ga.

[21] Appl. No.: 830,416

[22] Filed: Sep. 6, 1977

Related U.S. Application Data

[60] Division of Ser. No. 637,843, Dec. 5, 1975, abandoned, which is a continuation-in-part of Ser. No. 516,887, Oct. 22, 1974, Pat. No. 3,998,230.

[51] Int. Cl.² ............................................. A61B 17/00
[52] U.S. Cl. .......................................... 128/1 R; 3/1; 128/330
[58] Field of Search ...................... 128/330, 1 R; 3/1; 46/172; 132/53, 56

[56] References Cited

U.S. PATENT DOCUMENTS 3,003,155  10/1961  Mielzynski et al. ............. 128/330 X Primary Examiner—Robert W. Michell
Assistant Examiner—Michael H. Thaler
Attorney, Agent, or Firm—Robert B. Kennedy

[57] ABSTRACT

A method is disclosed for implanting hair into human skin comprising the steps of tieing a knot into a hair with the knot defining an interstice through which skin tissue may subsequently grow thereby anchoring the hair firmly in place, loading a needle by placing the hair knot in a hollow end of the needle and extending the hair from the knot through a notch formed in a surface of the needle end, inserting the loaded needle into the skin, and extracting the needle from the skin.

Apparatus is also disclosed for implanting hair having a bulbous end into human skin which apparatus comprises a tubular needle having a beveled end providing a pointed tip for piercing the skin and a notch formed in the beveled end through which the hair may extend with the bulbous hair end held within the tubular needle in engagement with an inner surface of the needle adjacent the beveled end notch.

A method is further described for determining an optimum size of an interstice defined by a knot on a hair to be implanted into human skin. The method comprises the steps of tieing a knot defining a spacial interstice of determined size in each of a plurality of hairs with the size of each knot interstice differing substantially from that of the interstices of the other knots; implanting each of the hair knots into the skin of a human; and subsequently exerting an extraction force on each hair and observing which hair required the greatest extraction force to be extracted without hair breakage.

2 Claims, 24 Drawing Figures

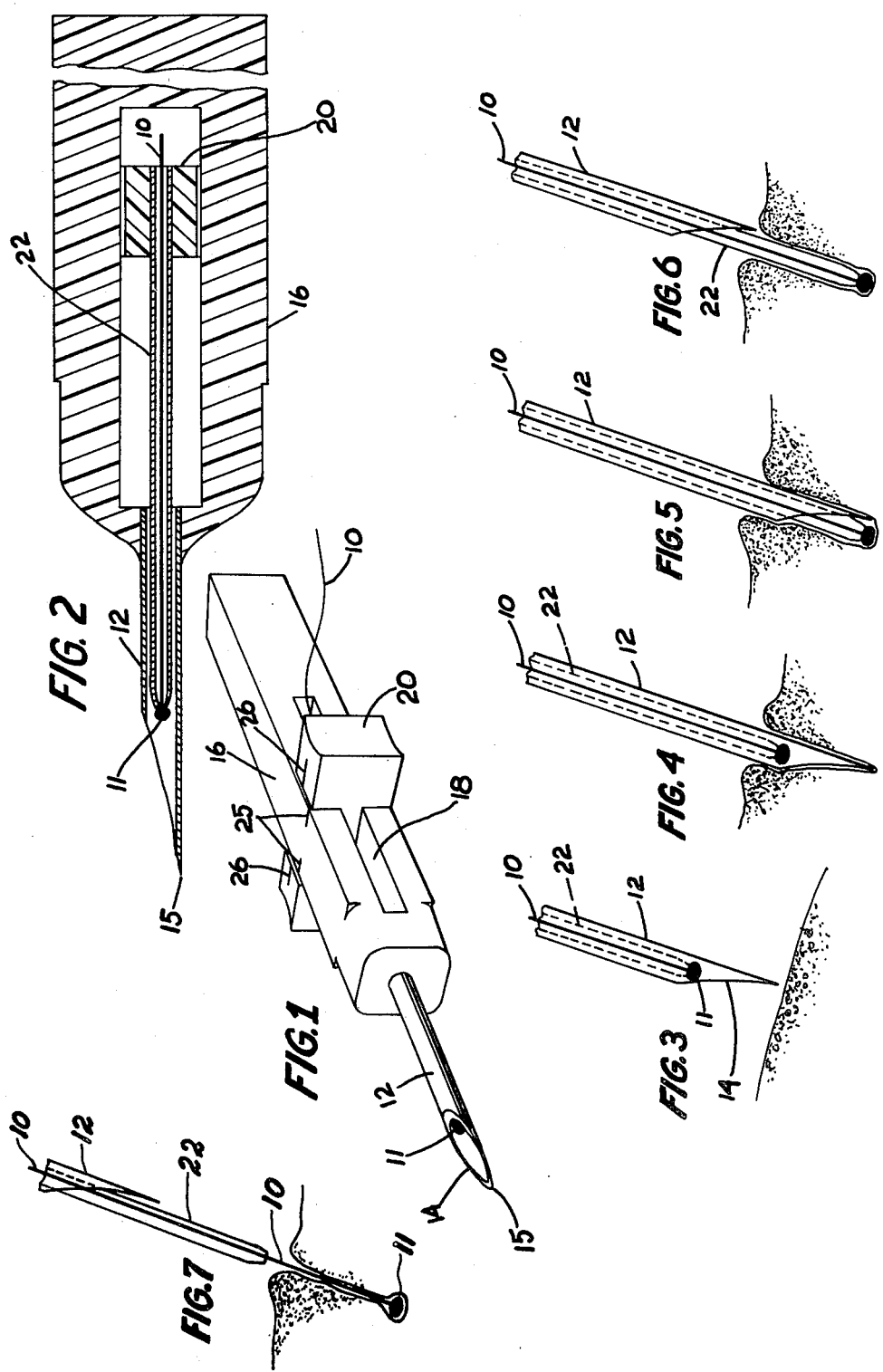

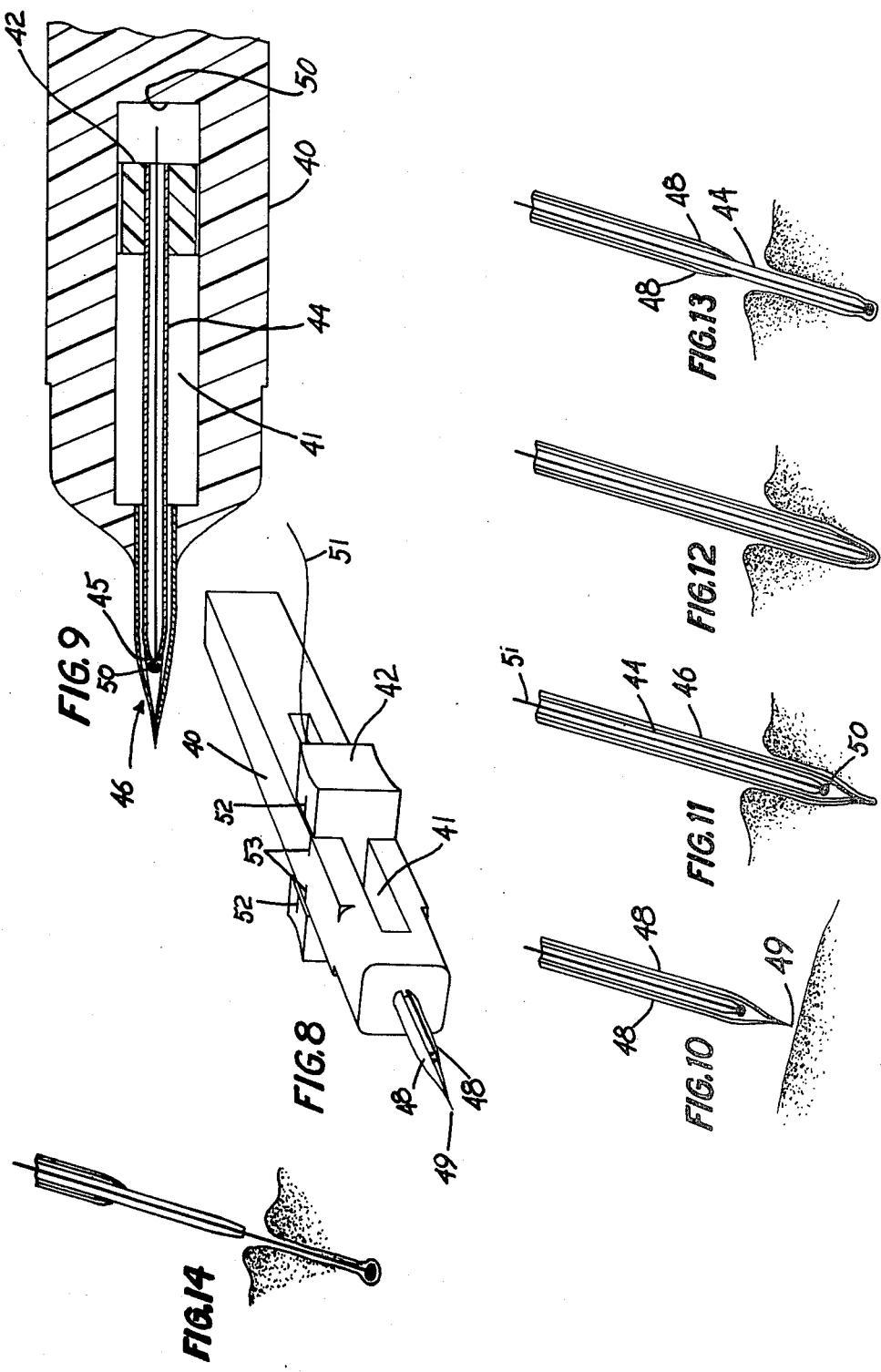

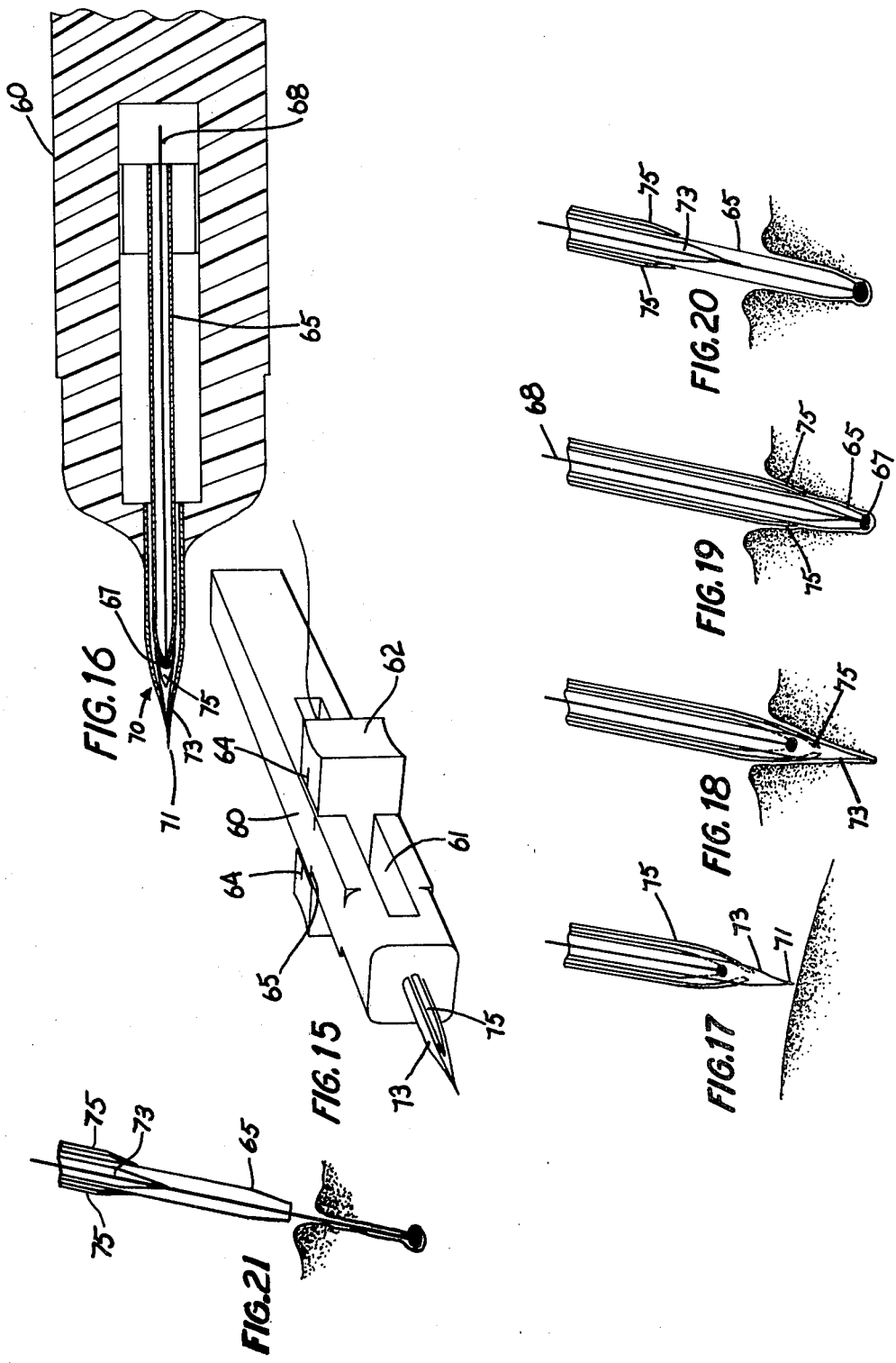

METHOD OF SIZING A HAIR ANCHOR

REFERENCE TO RELATED APPLICATION

This is a division of copending patent application Ser. No. 637,843 filed Dec. 5, 1975, now abandoned which is a continuation-in-part of patent application Ser. No. 516,887 filed Oct. 22, 1974, now U.S. Pat. No. 3,998,230.

BACKGROUND OF THE INVENTION

This invention relates to methods and apparatuses for implanting natural and synthetic hairs into human skin.

For many years efforts have been made to develop methods and devices for implanting artificial or natural hairs into the scalps of human beings in an effort to eliviate the appearance of baldness. For example, as early as 1913 a relatively complex hair implanting instrument was disclosed in U.S. Pat. No. 1,061,005. This apparatus included a mechanism for advancing a hair through a pair of flexible needle arms in timed sequence with the spreading of the arms. During this same year U.S. Pat. No. 1,059,631 also issued disclosing the use of a hook-type anchor secured to the end of a hair or to a set of hairs to provide a holding action when implanted into a human scalp. These earlier approaches were generally unsuccessful due to the tendency of the hairs to fall out.

In more recent years other methods and apparatuses have been developed in an attempt to improve the hair retention capability of artificially implanted hairs. In U.S. Pat. No. 3,003,155, for example, hair anchors are provided in the form of darts which may be used on either artificial media such as the heads of dolls or, it is claimed, on human scalps. In U.S. Pat. No. 3,062,214 electrically energized electrodes are used in an attempt to improve hair tenacity by creating scar tissue which encompasses the hair anchor. In U.S. Pat. No. 3,596,292 another hair anchor is proposed comprising a complex set of loops disposed below a percutaneous portion of the anchor. In U.S. Pat. No. 3,699,969 a group of hairs are placed inside a pair of telescoping needles with their ends tied together to form an anchor. All of these prior art methods and apparatuses have sought to attain the heretofore illusive goal of providing a relatively simple, practical and economic process of implanting hairs into the scalps of human beings which hairs remain firmly anchored in place for substantial periods of time. These prior attempts, however, have met with only nominal success. In addition, even where a percentage of the hairs implanted by the prior art methods have remained in place they have been anchored with varying and unpredictable degrees of tenacity. Where implanted too firmly efforts to uproot them subsequently after they have become color lightened and brittle through slow oxidation result in hair breakage leaving the hair anchor still implanted.

Accordingly, it is a general object of the present invention to provide improved methods and apparatuses for implanting hair into human skin.

More specifically, it is an object of the present invention to provide methods and apparatuses for implanting hair into human skin that remain firmly in place and securely anchored long after the implantation process is performed.

Another object of the invention is to provide a relatively simple method of implanting hair into human skin which method may be performed with facility with but minimal training.

Another object of the invention is to provide a method of implanting hair into human skin which does not tend to inflame or otherwise injure skin tissue.

Another object of the invention is to provide apparatuses for implanting hair into human skin of simple and economic construction and which may be readily cleaned for reuse.

Yet another object of the invention is to provide a method of sizing an anchor portion of a hair to be implanted in the skin of a human being.

SUMMARY OF THE INVENTION

In one form of the invention a method is provided for implanting hair into human skin. The method comprises the steps of tieing a knot into a hair with the knot defining an interstice through which skin tissue may subsequently grow thereby anchoring the hair firmly in place. A needle is loaded by placing the hair knot in a hollow end of the needle and extending the hair from the knot through a notch formed in a surface of the needle end. The loaded needle is then inserted in the skin and the needle extracted from the skin.

In another form of the invention a method is provided for determining an optimum size of an interstice defined by a knot on a hair to be implanted into human skin. The method comprises the steps of tieing a knot defining a spacial interstice of determined size in each of a plurality of hairs with the size of each knot interstice differing substantially from that of the interstices of the other knots; implanting each of the hair knots into the skin of a human; and subsequently exerting an extraction force on each hair and observing which hair required the greatest extraction force to be extracted without hair breakage.

In another form of the invention apparatus is provided for implanting hair having a bulbous end into human skin. The apparatus comprises a tubular needle having a beveled end providing a pointed tip for piercing skin and a notch formed in the beveled end through which the hair may extend with the bulbous hair end held within the tubular needle in engagement with an inner surface of the needle adjacent the beveled end notch.

BRIEF DESCRIPTION OF THE DRAWING

FIG. 1 is a perspective view of hair implanting apparatus embodying principles of the invention in one preferred form.

FIG. 2 is a cross-sectional view of the apparatus shown in FIG. 1.

FIGS. 3–7 are outline drawing views illustrating a sequence of operations in practicing a method of the present invention utilizing the apparatus shown in FIGS. 1 and 2.

FIG. 8 is a perspective view of hair implantation apparatus embodying principles of the invention in another form.

FIG. 9 is a cross-sectional view of the apparatus depicted in FIG. 8.

FIGS. 10–14 are outline drawing views illustrating a sequence of operation in practicing a method of the present invention utilizing the apparatus shown in FIGS. 8 and 9.

FIG. 15 is a perspective view of another hair implantation apparatus embodying principles of the invention.

FIG. 16 is a cross-sectional view of the apparatus depicted in FIG. 15.

FIGS. 17-21 are outline drawing views of a sequence of operation in practicing a method of the present invention utilizing the apparatus depicted in FIGS. 15 and 16.

DETAILED DESCRIPTION OF THE DRAWING

Figure 22:
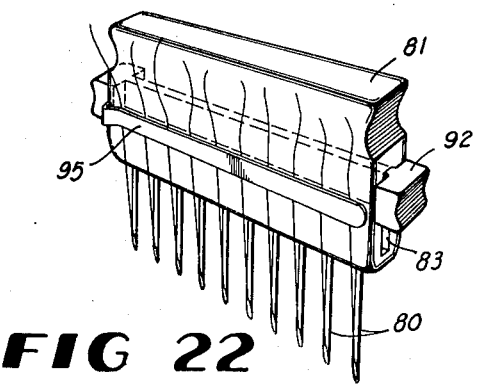
FIG. 22 is a perspective view of yet another device employing a plurality of ganged hair implantation apparatuses embodying principles of the invention.

Referring now in more detail to the drawing, there is shown in FIGS. 1 and 2 apparatus for implanting a hair 10 having a bulbous end 11 into human skin. The apparatus comprises a tubular outer needle 12 beveled at one end to form a chamfer 14 at an injection end thereof forming a sharp point 15. The outer needle is rigidly mounted to a handle 16 having a slot 18 formed through a central portion thereof. Within this slot is slidably mounted another handle or actuator 20 of H-shaped configuration to which a hollow inner needle 22 is rigidly mounted in frictionally sliding disposition within outer needle 12. The end of needle 22 distal actuator 20 is of bullet-shaped configuration and thus possesses a relatively blunt end in comparison with the sharp end of needle 12. A broken line 25 is marked upon the top of handle 16 and a line 26 marked atop actuator 20 to provide an indexing guide for positioning the two handles relative one another.

In performing the implantation operation a bulbous end is first formed on the synthetic or natural hair 10 with an interstice or passageway therethrough. Preferably, the bulbous end is formed by tieing a knot in the hair end with the knot defining an open space interstice. The size of the interstice has been discovered to be of great importance in creating proper anchoring strength. It formerly has been thought that the greater the holding power of the hair anchor the more successful the implant. This belief has been attributed to the fact that lack of success in former attempts at performing hair implants has been usually occasioned by rejection or insufficient tenacity of retention.

After many types of hair have been implanted for substantial periods of time they oxidize and thereby discolor, become brittle, and often split. Thus, after prolonged time periods it often becomes desirable to selectively remove some implants. However, where such are held too firmly in place the application of extraction forces only serve to break the hair leaving the bulbous hair end still implanted and a whisker at the skin surface.

The just described problem has been overcome by applicant by a sizing of the anchor interstice. This is preferably done by knotting the ends of a set of hairs of the type to be implanted with several hair knots having interstices of a differing sizes. This may be done by tieing a knot in one hair about a rod of one size and tieing knots in other hairs about rods of other, substantially different sizes. In this manner, for example, knots having interstices of 4, 6, 8, 10 and 12 mils may be tied on fine hairs, respectively. After this is done the hairs are implanted into the skin of the particular subject and the hair knot interstice sizes duly recorded. Some six weeks later each hair is gripped and pulled. That hair of the test group which requires the greatest force to extract with the bulbous end intact, that is with the hair not breaking, is identified and compared with the record. In this manner the optimum interstice size for that subject with that type hair is determined.

After the bulb has been formed on the hair end actuator 20 is positioned forwardly within slot 18 to provide ready access to the inner needle and the hair then inserted through the channel of inner needle 22 bringing the bulbous end onto the relatively blunt end of the needle. With the hair in place the actuator is moved rearwardly to the end of the slot by manual manipulation and handle 16 then urged towards the human skin bringing outer needle chamfer 14 into close proximity with the skin as shown in FIG. 3. The outer needle is then injected into the skin as shown in FIG. 4 creating the pit in the skin approximating the shape of chamfer 14. With the pit so formed actuator 20 is moved forwardly towards the skin until lines 26 are into registry with lines 25 which positions the relatively blunt end of the needle closely adjacent the outer needle tip 15 as shown in FIG. 5. In performing this operation the skin pit is enlarged slightly to accommodate the presence of the inner needle blunt end. Following this, actuator 20 is urged forwardly towards the end of the slot proximal outer needle end 15 while simultaneously urging handle 16 away from the skin which action serves to extract the outer needle from the skin pit while leaving the inner needle residing therewithin as shown in FIG. 6. This extraction of the outer needle causes the walls of the skin pit to close inwardly towards the inner needle which is then removed by moving handle 16 further away from the skin without necessarily imparting any further relative movement between the actuator and handle. This causes the inner needle also to be removed from the skin pit leaving the hair firmly implanted therewithin with the continually encroaching walls of the pit sealing about bulbous end 11. Subsequently, the skin tissue will also grow through the interstice rendering the implanted hair secure and tenaciously implanted.

Referring next to FIGS. 8 and 9 another embodiment of the invention is shown comprising a handle 40 having a slot 41 therein through which another H-shaped actuator 42 is slidably disposed in frictional engagement within handle 40 and with the actuator and handle again having indexing lines printed thereatop. To actuator 42 is rigidly mounted an inner, tubular needle 44 having a relatively blunt end 45 slidably disposed within an outer needle 46 that is rigidly secured to the handle. The inner needle, actuator and handle are thus seen to be of the same construction as that shown in FIGS. 1 and 2 whereas the outer needle 46 is seen to be of split injection type construction comprising a pair of arcuate prongs 48 spring biased into mutual engagement at their relatively sharp, mutually abutting ends 49.

In operation here actuator 42 is slid to the rear end 50 of slot 41 once needle 44 is loaded with a hair as previously described and handle 40 then moved towards the human skin to position outer needle sharp end 49 closely adjacent the skin as shown in FIG. 10. From this position handle 40 is urged forwardly injecting the split outer needle into the skin to form a skin pit in which both the outer needle and the blunt end portion of inner needle 44 are located. Next, actuator 42 is moved forwardly away from slot end 50 bringing lines 52 atop the actuator into registry with lines 53 on the handle. This action causes inner needle 44 to slide forwardly within the outer needle prongs 48. This action brings the outer peripheral portion of the blunt end of needle 44 into engagement with the insides of prongs 48 thereby forcing them radially outward from the coincident axes of the two needles. In this manner the prongs 48 are forced radially apart prior to any engagement of the bulbous end portion 50 of hair 51 seated upon the inner peripheral portion of the needle blunt end with the prongs. Thus, the centrally apertured annular portion of the blunt end serves both to support the bulbous end 50 of the hair and to cam apart the prongs of the outer needle.

At this point the relative positions of the two needles within the skin pit are depicted in FIG. 12. Next, actuator 42 is urged to the opposite end of the slot from slot end 50 while handle 40 is simultaneously moved away from the skin. This causes the outer needle prongs 48 to slide up upon the outside of inner needle 44 thereby extracting the outer needle from the skin pit as shown in FIG. 13. Finally, the handle 40 is moved further away from the skin without necessarily imparting any further relative movement between the two needles thereby extracting the inner needle too from the skin pit leaving the hair firmly implanted.

Referring next to FIGS. 15 and 16, yet another embodiment of the invention is shown comprising a handle 60 having a slot 61 in which is slidably disposed an actuator 62 of generally H-shaped configuration having a pair of aligned marks 64 thereatop adapted to be aligned with lines 65 atop handle 60. As in the previously described embodiments actuator 62 supports a tubular needle 65 having a relatively blunt end for supporting a bulbous end 67 of a hair 68. Handle 60 supports a split-injection type needle 70 having a relatively sharp end 71. This split-injection needle comprises two arcuate, resilient prongs 73 spring biased into mutual engagement at points 71 plus a second pair of arcuate, resilient prongs 75 having their ends spaced apart and longitudinally offset from points 71 of the other pair of prongs. The inner and outer needles may be moved relative to one another by the movement of actuator 62 within slot 61 as described in the discussion of the previous embodiments.

The relative positioning of the needles within the skin is illustrated in FIGS. 17–21 wherein in FIG. 17 outer needle end 71 is shown positioned closely adjacent the skin and in FIG. 18 injection of both pairs of outer needle prongs has been completed to create a skin pit thereabout. That the two pairs of prongs separate along planes oriented normal to one another serves to create a generally cylindrical pit in the skin which subsequently minimizes hair end contact with the pit walls. Following this inner needle 65 is advanced into engagement with prongs 75 forcing them outwardly apart as shown in FIG. 19. Continuation of this advancement of the inner needle enlarges the cavity somewhat in positioning the bulbous end 67 of hair 68 adjacent sharp point 71 of the outer needle. In this the relatively blunt end of the inner needle also serves to force apart the resilient prongs 73 enabling the bulbous end of the hair to be seated therebetween. Next, the outer needle is pulled away from the skin over the surface of the inner needle the presence of which continues to separate both pairs of the spring biased prongs of the outer needle as illustrated in FIG. 20. Finally, inner needle 65 is also pulled from the skin pit as shown in FIG. 21 leaving the hair planted firmly within the skin.

Figure 24:
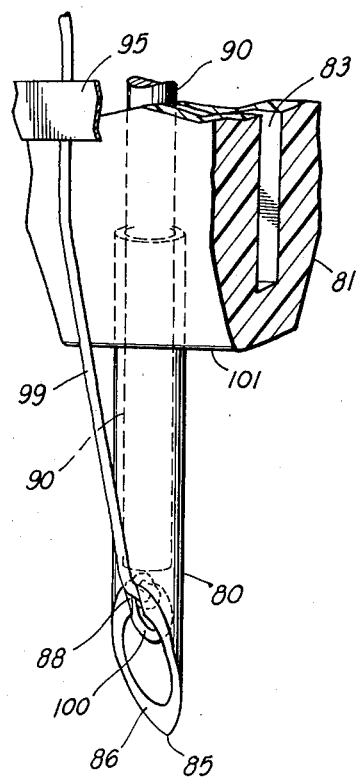
FIG. 24 is an enlarged view in perspective of a portion of the apparatus illustrated in FIG. 23.
Figure 23:
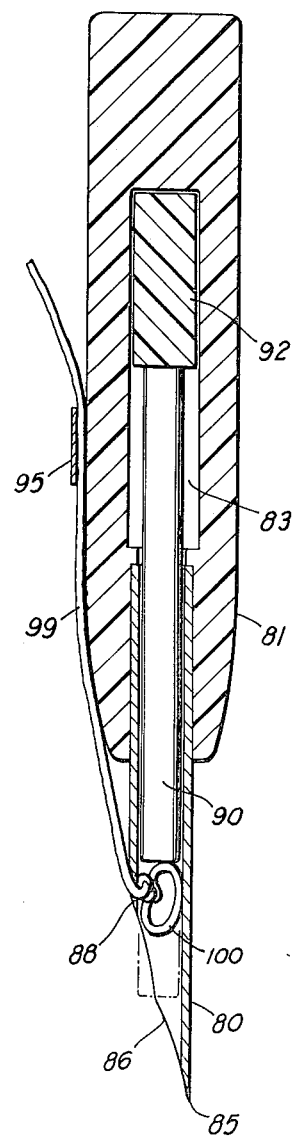
FIG. 23 is a side elevational view of one of the ganged apparatuses shown in FIG. 22.

Referring next to FIGS. 22–24 there is shown yet another embodiment of the invention comprising a tubular, substantially cylindrical needle 80 such as a 25 gauge "Yale" type hypodermic needle manufactured by Becton, Dickinson and Company of Rutherford, New Jersey. The needle is rigidly secured to a handle 81 formed with a slot 83. The end of the needle distal the handle is beveled to form a pointed needle tip 85 and a chamfer 86. A notch 88 is formed in that portion of the chamfer located radially opposite the needle tip. Preferably, the notch extends almost completely through the chamfer from the needle bore to the cylindrical, exterior surface of the needle. The notch may be formed by sawing with a 3 mil carbon-steel wire passed through the needle bore and looped over the chamfer.

A push rod 90, preferably of solid cylindrical construction such as a 9 mil metallic, flexible wire, is slidably disposed within needle 80 and secured to a second handle or actuator 92. This actuator is of generally H-shaped configuration and is slidably positioned within slot 83 of handle 81. A metal clip 95 is mounted at one end to handle 81 with the clip body spring biased into contact with an external surface thereof.

For operation the just described apparatus is loaded with a hair 99 having a bulbous end 100 preferably formed with an open interstice as hereinbefore described. Loading is accomplished by simply placing the hair in chamfer slot 88 with the bulbous hair end positioned in the hollow end of needle 80 adjacent the chamfer. Preferably, the hair is also held to the surface of handle 81 by passing it between the handle and clip or other holding means such as adhesive tape. The loaded needle is then injected into the skin of a human with handle 92 located at the upper end of slot 83 as shown in FIG. 23. In doing this the lower end 101 of handle 81 may be brought into contact with the skin which end thereby serves as an indexing means and stop. Clip 95 may then be raised and handle 81 drawn away from the skin surface while handle 92 is simultaneously held stationary with respect to the skin. This action causes rod 90 to urge the bulbous end of the hair out of the end of needle 80 as it withdraws. Alternatively, the push rod may be eliminated in which case the hair merely slides out of chamfer slot 88 as the needle is withdrawn. The use of the rod, however, is preferred for better operational control. After needle 80 is extracted rod 90 is also extracted leaving the bulbous end of the hair implanted.

The just described embodiment of FIGS. 22-24 has been found to yield excellent results with virtually no residual, observable scarring. This lack of scarring and skin irritation is believed to be attributable to the fact that a single needle may be extremely small in diameter where another, tubular needle does not have to be slidably disposed therewithin as in the previously described embodiments. Indeed, only the end of the single needle here, adjacent the chamfer, need be hollow where a push rod is not employed. Furthermore, where a set of the needles are ganged together, as shown in FIG. 22, several hairs may be simultaneously implanted, enhancing the speed of operation.

It should be understood that the just described embodiments merely serve to illustrate principles of the invention in preferred forms. Many modifications may, of course, be made thereto without departure from the spirit and scope of the invention as set forth in the following claims.

I claim:

1. A method of sizing an anchor portion of a hair to be implanted in the skin of a human, said method comprising the steps of:

(a) tieing a knot defining a special interstice of determining size in each of a plurality of hairs with the size of each knot interstice differing substantially from that of the interstices of the other knots;
(b) implanting each of the hair knots into the skin of a human; and subsequently
(c) exerting an extraction force on each hair and observing which hair required the greatest extraction force to be extracted without hair breakage.

2. The method of claim 1 wherein step (a) includes the step of tieing the knot in each hair about a rod of size approximating said determined size and then removing the knot from the rod.

* * * * *